United States Patent
Blunk (10) Patent No.: US 10,495,583 B2
(45) Date of Patent: Dec. 3, 2019

(54) VIDEO CAMERA INSPECTION SYSTEM

(71) Applicant: Quanta Associates, L.P., Houston, TX (US)

(72) Inventor: Ryan Michael Blunk, Thousand Oaks, CA (US)

(73) Assignee: Quanta Associates, L.P., Houston, TX (US)

( * ) Notice: Subject to any disclaimer, the term of this patent is extended or adjusted under 35 U.S.C. 154(b) by 15 days.

(21) Appl. No.: 15/813,733

(22) Filed: Nov. 15, 2017

(65) Prior Publication Data

US 2018/0136144 A1  May 17, 2018

Related U.S. Application Data

(60) Provisional application No. 62/422,561, filed on Nov. 15, 2016.

(51) Int. Cl.
| | |
|---|---|
| *G01N 21/952* | (2006.01) |
| *G01N 21/01* | (2006.01) |
| *H04N 5/225* | (2006.01) |
| *G06T 7/00* | (2017.01) |
| *H04N 5/247* | (2006.01) |
| *G03B 17/08* | (2006.01) |

(52) U.S. Cl.
CPC .......... *G01N 21/952* (2013.01); *G01N 21/01* (2013.01); *G06T 7/0004* (2013.01); *H04N 5/2253* (2013.01); *H04N 5/2256* (2013.01); *G01N 2021/0106* (2013.01); *G03B 17/08* (2013.01); *H04N 5/247* (2013.01)

(58) Field of Classification Search
CPC .................. G01N 21/952; G01N 21/01; G01N 2201/0212; G01N 2021/0106; G03B 17/561; G03B 15/03; G03B 37/04; G03B 17/08; H04N 5/2256; H04N 5/2253; H04N 5/247; G06T 7/0004
USPC .......................................................... 348/81
See application file for complete search history.

(56) References Cited

U.S. PATENT DOCUMENTS 3,667,515 A * 6/1972 Corey ...................... E02D 9/04
                                                   83/743
3,693,676 A * 9/1972 Burch ................ B23D 57/0084
                                                   30/381

(Continued)

FOREIGN PATENT DOCUMENTS

CN      2017-879592     *  5/2017   ............ F16M 11/04

*Primary Examiner* — Marnie A Matt
(74) *Attorney, Agent, or Firm* — Donald L. Bartels; Bartels Law Group (57) ABSTRACT

The system enables remote inspection of an object, such as an underwater steel pile, using a plurality of video cameras. The cameras are positioned on a frame along a plane substantially perpendicular to the axis of the object and spaced apart so as to enable inspection of the circumference of the object. Moving the frame along the surface of the object enables a video of the entire surface area of the object to be made. A plurality of wheels are mounted to the frame to provide rolling contact with the surface of the object and to cause the cameras to remain a fixed distance from the surface of the object. A plurality of springs are mounted between the frame and the wheels to further ensure smooth movement of the frame. A plurality of lights mounted to the frame illuminate the surface of the object during the inspection process.

10 Claims, 8 Drawing Sheets

(56) References Cited

U.S. PATENT DOCUMENTS

| | | | | |
|---|---|---|---|---|
| 5,947,051 | A * | 9/1999 | Geiger | B62D 57/00 |
| | | | | 114/222 |
| 6,512,536 | B1 * | 1/2003 | Ross | G01B 11/105 |
| | | | | 348/61 |
| 8,525,124 | B2 * | 9/2013 | Atwood | B62D 55/12 |
| | | | | 250/394 |
| 9,863,891 | B1 * | 1/2018 | Lara Magallanes | |
| | | | | G01N 21/952 |
| 2017/0247092 | A1 * | 8/2017 | Foster | B63C 11/52 |
| 2018/0306749 | A1 * | 10/2018 | Ruttanasupa | G01M 3/40 |

* cited by examiner

VIDEO CAMERA INSPECTION SYSTEM

CLAIM OF PRIORITY

This application claims priority to U.S. Provisional Patent Application Ser. No. 62/422,561, filed on Nov. 15, 2016, the entirely of which is incorporated herein by reference.

FIELD OF THE INVENTION

The invention relates to video came based inspection systems. One use of such a system is for the inspection of structures in difficult to access areas, for example, the underwater inspection of piers or other types of piles using a plurality of video cameras mounted on a frame.

BACKGROUND OF THE INVENTION

Currently, in one application, an underwater human dive team provides quality control (QC) inspections of the epoxy coating applied to steel piles. In one example, 267 hollow steel piles (30"-36"×120' long) were installed in the ocean. A marine epoxy coating with a 75 year design life was applied to each pile prior to pile driving. Inspection of the coating on each pile after the pile was driven into place was previously performed by underwater quality control divers.

SUMMARY OP THE INVENTION

The present invention is a method and system for the inspection of the surfaces of objects such as pipes or underwater piles using one or more video cameras mounted on a supporting frame. According to one embodiment, the invention enables remote inspection of the epoxy coating on 36" diameter steel piles positioned under water using an array of spaced apart remotely operated video cameras. The present invention according to this embodiment replaces the use of an underwater human dive team to provide quality control (QC) inspections. The cameras are spaced horizontally on a frame with respect to the axis of the object in a way to allow for simultaneous inspection of the entire circumference of a pile. The method in which the cameras are raised and lowered across the vertical surface of the pile ensures that no areas of coating are missed, and thus the present invention enables a complete QC inspection of the pile to be performed by the generation of high quality video images of the entire surface of the pile along its entire length.

In an alternate embodiment, skateboard wheels, or a similar combination of rollers, are mounted to the frame and sized to provide rolling contact with the surface of the object for enabling the cameras to remain a substantially fixed distance from the surface of the object. This enables the focal length of the cameras to also remain fixed, and further enables the frame to move smoothly along the surface of said object. In certain embodiments, the composition of the rollers is selected to ensure that the pile's coating is not damaged while the frame is being moved up and down the pile being inspected and so that the rollers are resistant to deterioration in applications where the system is being used in a harsh environment. A plurality of springs are preferably mounted between the frame and the wheels to enable the array of cameras to more consistently remain a fixed distance from the pile. Strategically placed lights are mounted to the frame to provide overlapping illumination of the surface of the object throughout the inspection process. In both scenarios, the video feed can be stored on the cameras SD cards (removable storage) or can be live streamed to a remote location, e.g., a display located on the surface of the sea, for viewing in real time.

According to one embodiment of the invention, a video camera inspection system for remotely inspecting the surface of an object comprises: a frame sized to move along the length of said object: a plurality of cameras attached to the frame in spaced apart locations along a plane substantially perpendicular to the axis of the object, for enabling video recording of the entire circumference of said object as said frame is moved along the object; a plurality of lights attached to said frame for illuminating the surface of said object; a plurality of wheels attached to said frame sized to provide rolling contact with the surface of the object for enabling the cameras to remain a substantially fixed distance from the surface of the object and for enabling the frame to move smoothly along the surface of said object; and means for causing the fame to be selectively moved along the length of said object to enable a complete video recording of the surface of the object to be made.

According to another embodiment of the invention, a method for inspecting the surface of an object comprises: positioning a fame with respect to the surface of said object, said frame defining a plane substantially perpendicular to the axis of said object, said fame including a plurality of video cameras attached to the frame in spaced apart locations on said plane; remotely controlling the movement of said frame along the length of said object; causing said cameras to make a video recording of the entire circumference of said object as said frame is moved along the object; positioning a plurality of lights to said frame for illuminating the surface of said object; and fastening a plurality of wheels to said frame sized to provide rolling contact of said frame with the surface of the object, for enabling the cameras to remain a substantially fixed distance from the surface of the object and for enabling said frame to move smoothly as said frame is moved along the surface of said object.

Advantages of the present invention include the following:

1). Increased Safety. First and foremost, this invention virtually eliminates the need to expose humans (in this case underwater divers) to the hazards of underwater diving in order to complete government required inspections of pile coatings. Removing human exposure to the risks and dangers in this construction workplace is an unquantifiable advantage of using a system of remotely operated cameras. These dangers could include boat/ship traffic, extreme ocean weather conditions, marine mammals and wildlife, construction activities, and anything else hazardous to human health.

2). Cost savings. Operating costs for using remotely operated cameras are a fraction of what it costs for a comparable human dive team. Once the system has been constructed, there are minimal labor and maintenance costs.

3). Project scheduling gains. Time is money in construction, and this invention proved a faster and more efficient use of time versus utilization of underwater divers. In order to build the pier in the example above, hollow steel piles were driven into the ocean floor to act as the foundation for the pier concrete support structure. With a limited pile driving window, the speed at which piles could be driven is of utmost importance. Contract requirements in this case also required inspection of coating to occur within seven days of driving a pile into the seabed. This can put a severe damper on the speed at which a similar project could progress. The underwater camera inspection system according to the present invention allows for piles to be continuously driven, even while coating inspections were occurring nearby. This would not have been possible with human divers conducting the inspections as dive inspection rules often prohibit above water work from being conducted in the vicinity of divers. The ability to accomplish construction activities concurrently saves time, which in turn can yield additional cost savings. Additionally, the remotely operated cameras operate at a much more efficient pace and can inspect piles at an overall faster pace than human divers.

According to another embodiment of the present invention, a method for inspecting an object comprises moving a static arrangement of cameras down the surface of the object (e.g., a pile) in a dynamic environment such as the ocean. The invention provides the ability to meet critical pile driving deadlines while limiting underwater exposure hours for divers. The invention also eliminates fall and impact hazards to underwater divers. The present invention cuts the cost of inspecting the piles while improving safely and quality.

The above, and other objects, features and advantages of the present invention will become apparent from the following description read in conjunction with the accompanying drawings, in which like reference numerals designate the same elements.

BRIEF DESCRIPTION OF THE DRAWINGS

The features, advantages, and benefits of the present invention will become more apparent from the following description taken in conjunction with the accompanying drawings, which are presented solely for exemplary purposes and not with the intent to limit the invention thereto, and in which.

Reference symbols or names are used in the Figures to indicate certain components, aspects or features shown therein, with reference symbols common to more than one Figure indicating like components, aspects or features shown therein.

DETAILED DESCRIPTION OF THE INVENTION

According to one embodiment of the invention, an array of video cameras enables remote underwater inspection of an epoxy coating applied to 36" diameter steel piles. The system preferably uses a plurality of remotely operated cameras mounted on a rigid frame or jig. The frame is preferably either circular or square along or in a plane (e.g. a single plane or the same plane) perpendicular to the axis of the pile.

Figure 1:
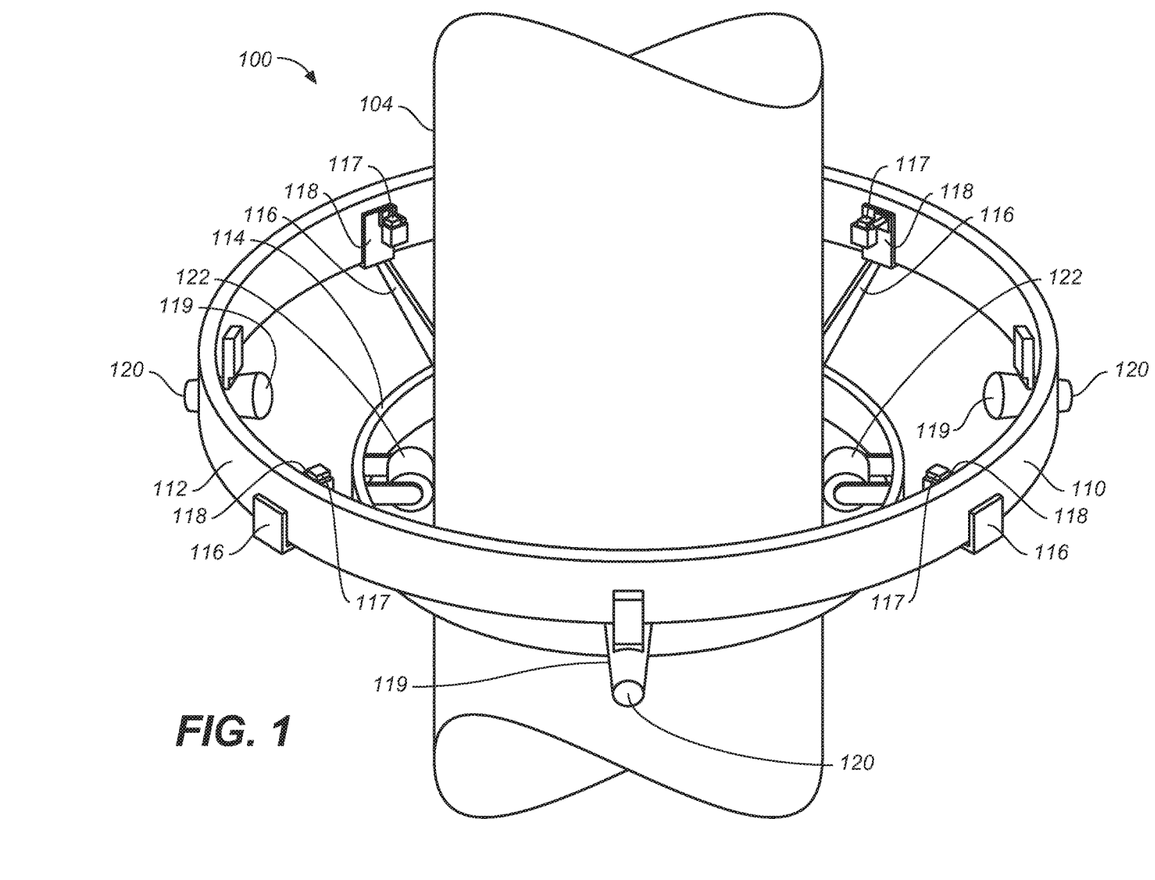
FIG. 1 illustrates a perspective view of one embodiment of an underwater camera inspection system according to the present invention positioned around a pile and enabled by a winch to move up and down the pile.

FIG. 1 illustrates one embodiment of a camera inspection system 100 according to the present invention. In the embodiment shown in FIG. 1, system 100 is configured for use as an underwater camera inspection system and is positioned around a pile 104 and enabled to move up and down the pile 104 by a winch mounted at the top of the pile 104 (not shown). As seen in FIG. 1, in the embodiment shown, the frame 110 comprises two circular pipes 112 and 114 offset from one another by a plurality of legs 116. Pipes 112 and 114 are preferably made of stainless steel, other materials such as aluminum and carbon fiber could be used. Non-oxidizing or rustproof materials are best suited for salt water use of camera inspection system 100 when it is used in salt water. Four video cameras 117 are mounted to steel pipe 112 at points 118. Cameras 117 are spaced at equal intervals around frame 110 to enable the cameras 117 to be in the same horizontal orientation (e.g. the same plane) with respect to the pile 104 to enable the entire circumference of pile 104 to be captured on video at the same time. Four underwater diving lights 119 are mounted to steel pipe 112 at spaced apart points 120 to provide overlapping illumination of the coating of pile 104 throughout the inspection process as camera inspection system 100 moves vertically up, down or both about an outside of pile 104. A plurality of wheels 122 are mounted to steel pipe 114 to enable the frame 110 to move unimpeded up or down pile 104 in such a way that the distance between each camera 117 remains substantially constant. The wheels 122 are offset from cameras 117 to ensure that the wheels 122 do not interfere with the view of the cameras during videoing of the pile. Videoing of pile 104 may or may not be recorded tor subsequent viewing or verification by an inspector, for example.

As can be seen, the method according to the present invention comprises the raising and lowering of the inspection system 100 across the entire vertical, exterior surface of the pile to ensure that no areas of the pile's coating are missed during inspection of the pile.

Figure 2:
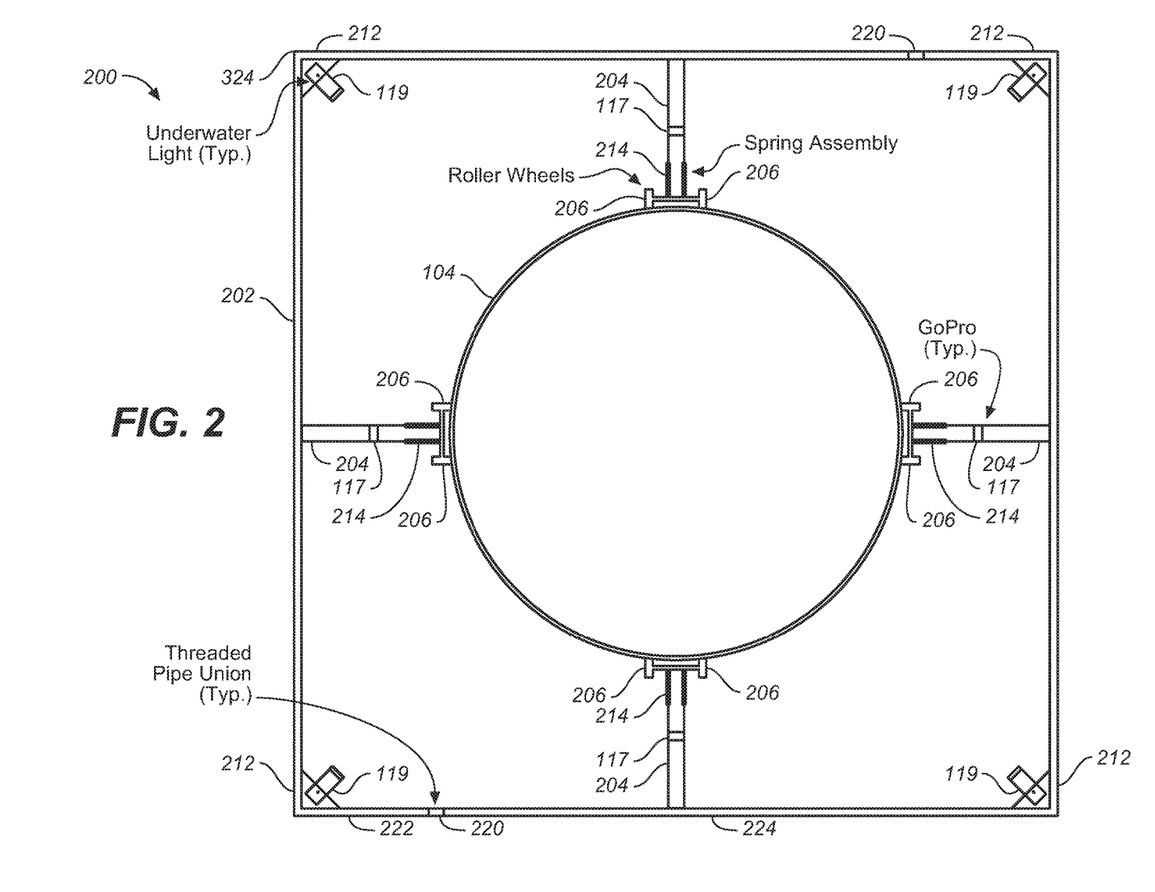
FIG. 2 is a top view of another embodiment of an underwater camera inspection system according to the present invention having a square frame.

FIG. 2 is a top view of another embodiment of an underwater camera inspection system 200 for inspecting pile 104 according to the present invention. As seen in FIG. 2, the frame 202 is a square shaped stainless steel pipe, but the material may be aluminum, carbon fiber or other material depending upon the application of underwater camera inspection system 200. One end of legs 204 are attached to the sides of the frame 202 as shown, and wheels 206 are attached to the other end (e.g. the opposite end) of legs 204. In a preferred embodiment, skateboard wheels are used for wheels 206 to ensure that the coating is not damaged while the pile 104 is being inspected. The use of two wheels at the end of each leg helps ensure that the frame remains stable during the raising and lowering of system 200. Wheels 206 may be made from a variety of non-marking, non-abrasive materials that also permit a surface of wheels 206 to maintain grip and rolling contact with an exterior surface of pile 104. Some materials include polyurethane, rubber, and plastic. Wheels may be resilient to withstand repeated handling, use, or exposure to corrosive environments.

In the embodiment shown, four cameras 117 are positioned with one fastened to each of the legs 204. Each camera is equally and circumferentially spaced apart from an adjacent camera, and as depicted in FIG. 2, in a circular or arcuate configuration. Other configurations, given the application or exterior geometry of a pile, are conceivable. The essential aspect to maintain is a relatively fixed offset from the pile in order not to distort the images or video obtained from the cameras. If there is distortion potential defects may be missed which would negate the benefits of using this for inspection purposes. In this arrangement, the cameras 117 are able to capture the entire circumference of pile 104 on video at the same time. Four underwater diving lights 119 are mounted to frame 202 at spaced apart points to provide overlapping illumination of the pile 104's coating throughout the inspection process. In this embodiment, as shown, the diving lights are mounted at the corners 212 of frame 202.

A plurality of springs 214 are also used in the embodiment shown in FIG. 2, one each mounted between each, of the wheels 206 and legs 204, and function to enable the array of cameras to more consistently remain a fixed distance from the pile and to dampen any vibration between the frame 202 and pile 104 caused by movement of the frame in and through the water, ocean currents, etc.

According to the present invention, various ways are known in the art to enable the underwater camera inspection system 200 to be assembled around a structure such as pile 104. As seen in FIG. 2, frame 202 includes two threaded pipe sections 220. Using these threaded pipe sections, the two halves 222 and 224 of frame 202 can be disassembled and separated from each other for enabling the system 200 to be easily installed around a pile 104.

Figure 3:
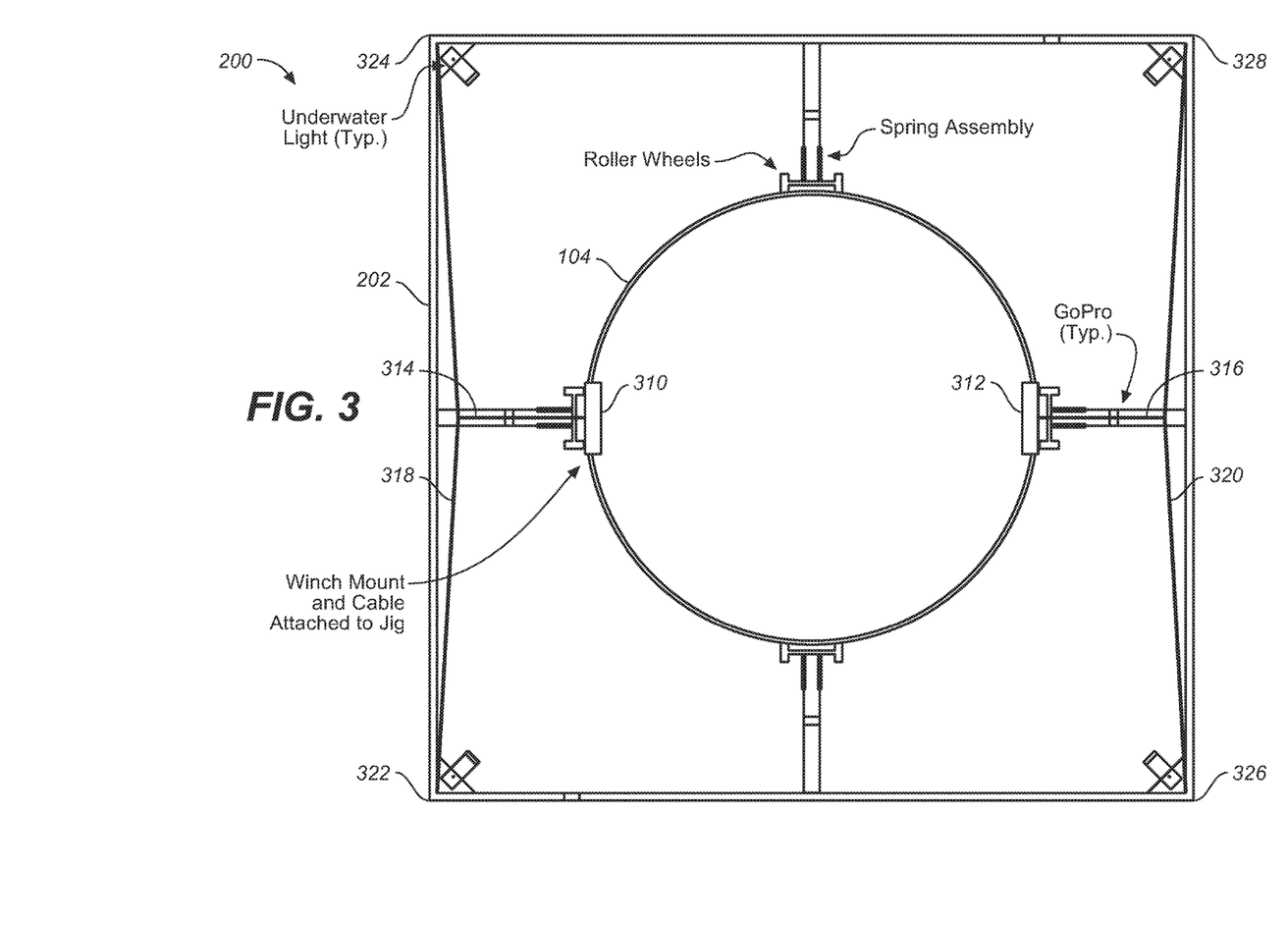
FIG. 3 is a top view of the system of FIG. 2 showing schematically the mounting of one embodiment of a winch system to the top of the pile and one embodiment of cabling between the winch system and the frame of the camera inspection system.
Figure 4:
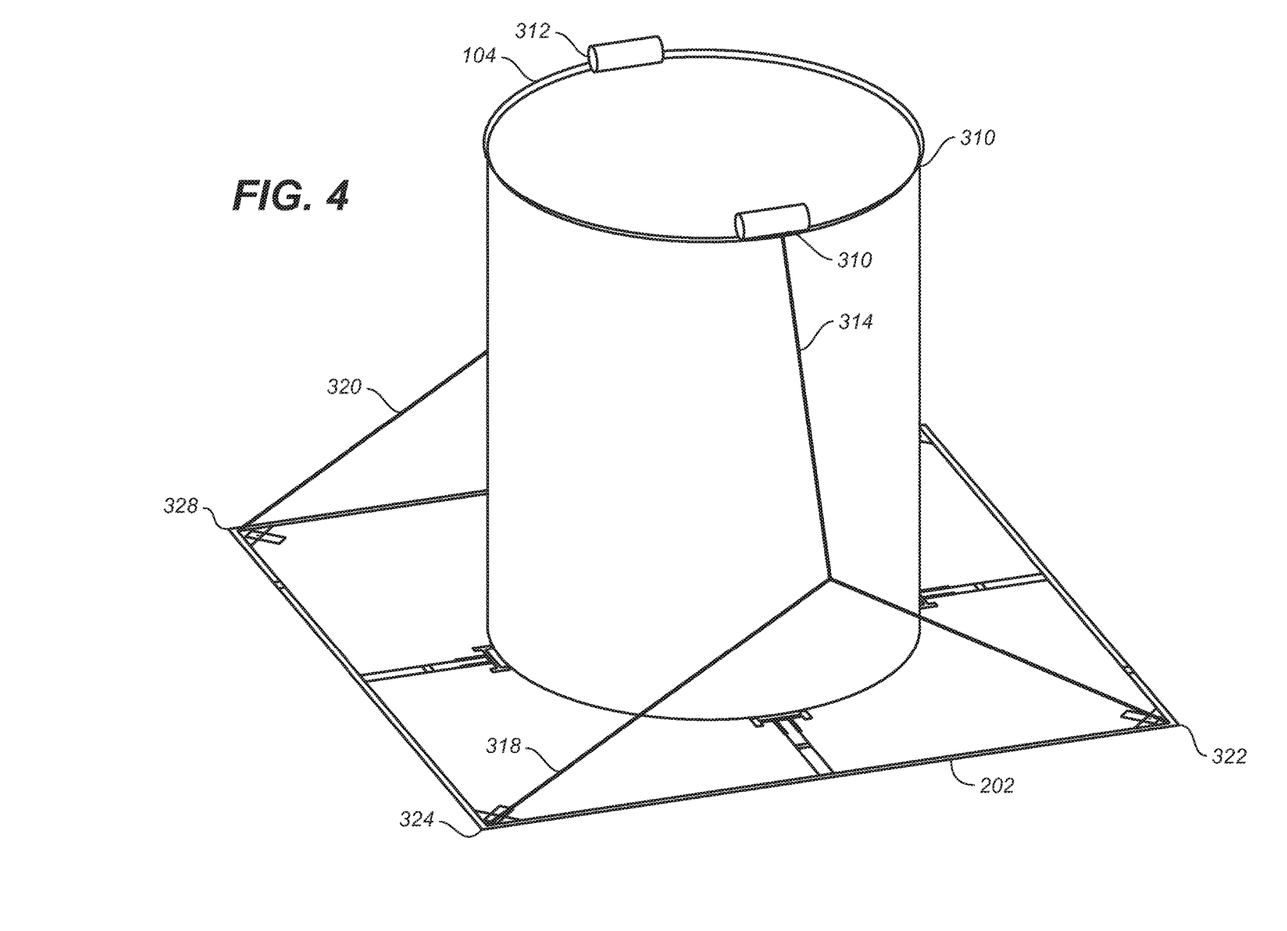
FIG. 4 is a perspective view of the winch system and cabling shown in FIG. 3.

FIG. 3 is a top view of the system 200 of FIG. 2 showing schematically the mounting of one embodiment of a winch system to the top of the pile and one embodiment of cabling between the winch system and the frame 202 of the camera inspection system 200. As seen in FIG. 3, two winches are preferably used. They are schematically shown as 310 and 312. Winches 310 and 312 are mounted in a conventional manner at the top of pile 104 and are used to mechanically raise and lower system 200 along the pile 104. For this purpose, each winch 310, 312 functions to reel out and reel in a stainless steel cable, shown at 314 and 316, respectively. In one embodiment, die steel cable is ⅛ inches in diameter. Additional cables 318 and 320 are attached at the corners of frame 202. Cable 318 is attached to corners 322 and 324, and cable 320 is connected to corners 326 and 328. An equal amount of slack is provided in each cable 316 and 320 to enable cables 314 and 316 to be attached in a conventional manner to respective cables 318 and 320, e.g., with a cable clip. FIG. 4 is a perspective view of the winches 310 and 312 and cables 314, 316, 318, and 320 shown in FIG. 3.

Figure 5:
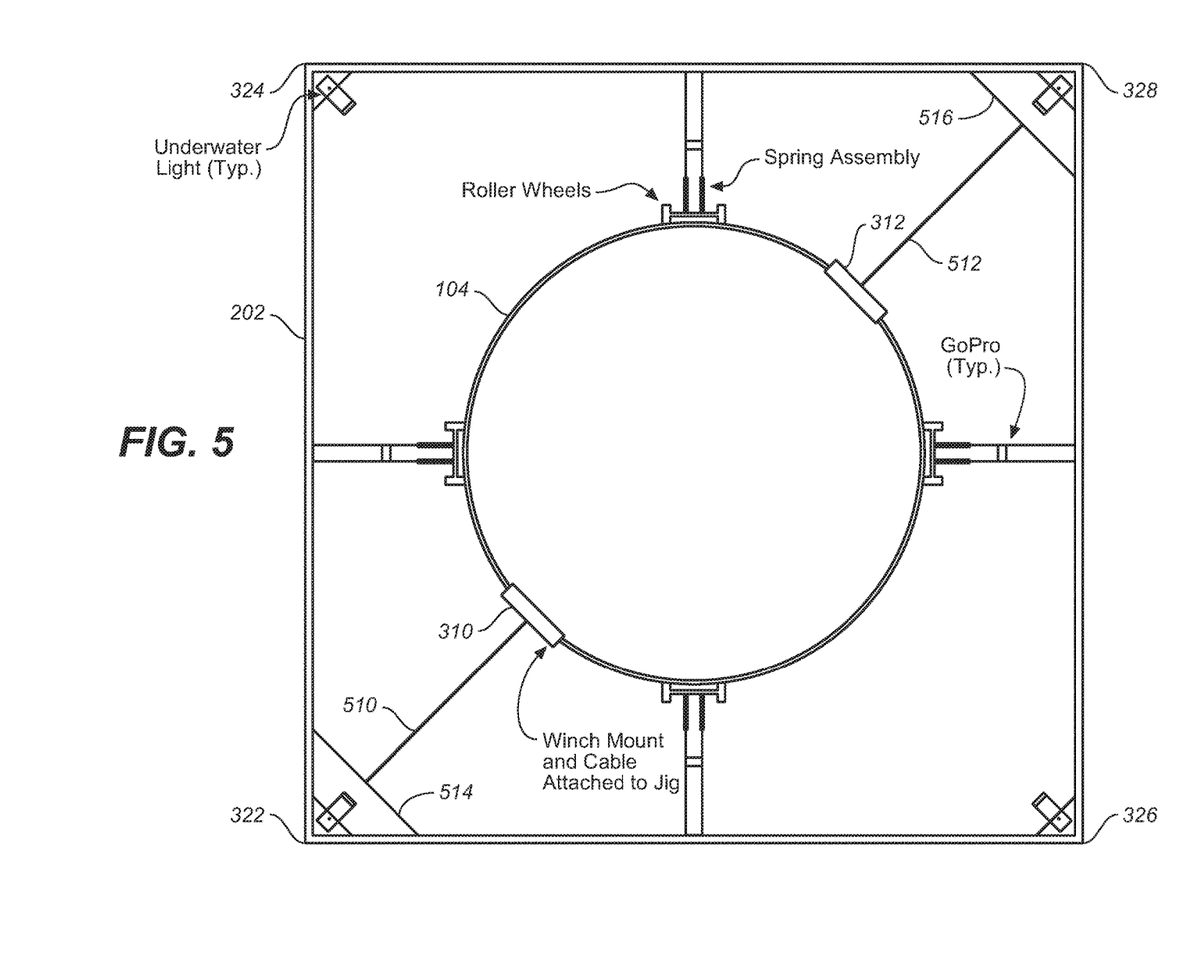
FIG. 5 is a top view of the system of FIG. 2 showing schematically the mounting of another embodiment of cabling between the winch system and the frame of the camera inspection system.
Figure 6:
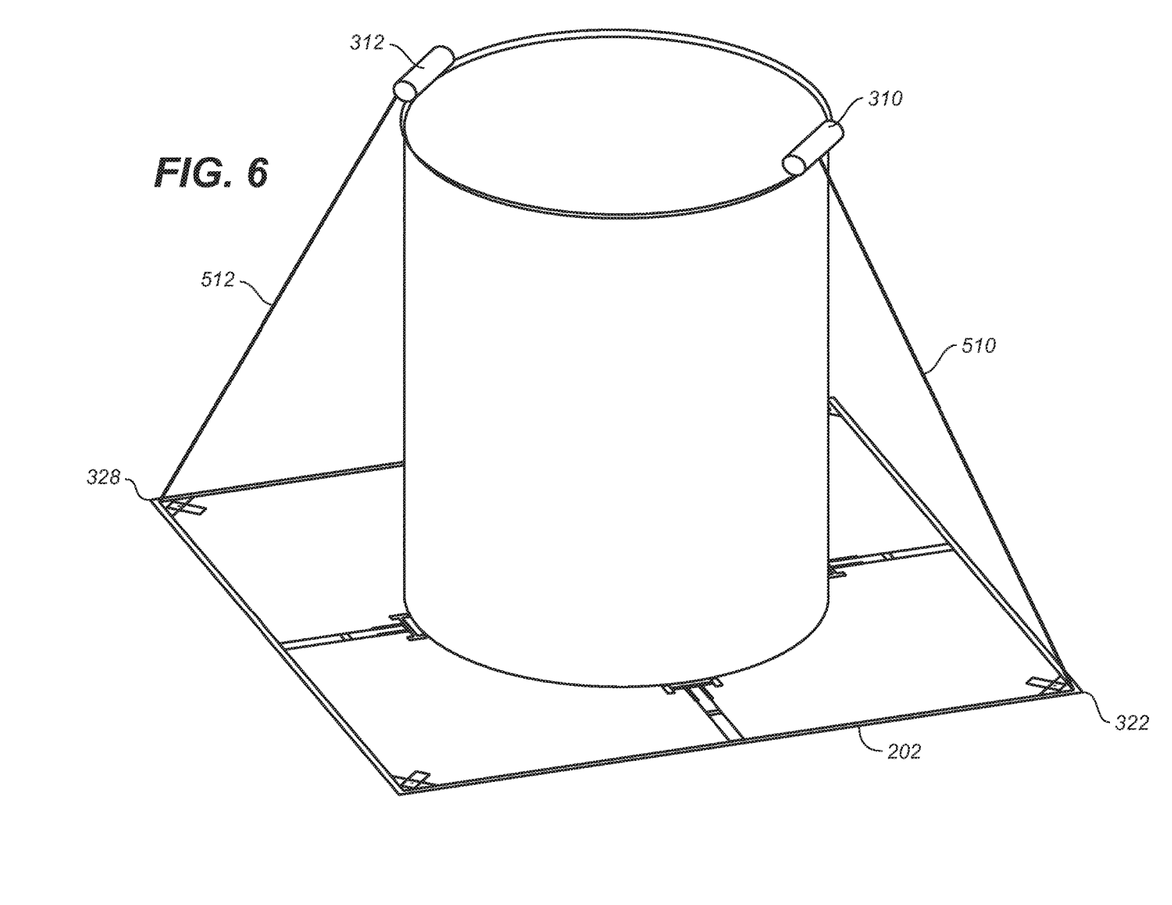
FIG. 6 is a perspective view of the winch system and cabling shown in FIG. 5.

FIG. 5 is a top view of the system 200 of FIG. 2 showing schematically the mounting of another embodiment of cabling between the winches 310 and 312 and the frame 204 of the camera inspection system. As seen in FIG. 5, winch 310 includes a stainless steel cable 510 and winch 312 includes a stainless steel cable 512. Cable 510 is either connected directly to the corner 322 of frame 202 or it is clipped to a cable 514 that is attached to frame 202 on each side of corner 322. In the same fashion, cable 512 is either connected directly to the corner 328 of frame 202 or it is clipped to a cable 516 that is attached to frame 202 on each side of corner 328. FIG. 6 is a perspective view of the winches 310 and 312 and cables 510 and 512 shown in FIG. 5. FIG. 5 shows the connection of cables 510 and 512 to corner cables 514 and 516, respectively, while FIG. 6 shows cables 510 and 512 connected directly to frame 202 at corners 322 and 328, respectively.

Figure 7:
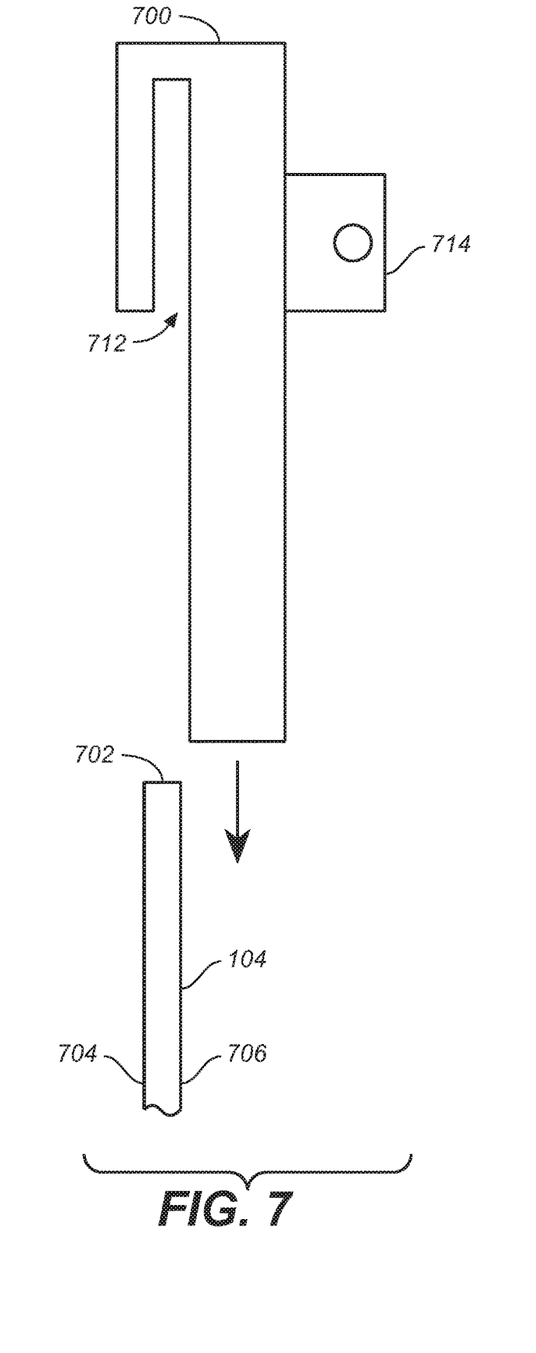
FIG. 7 is a side view of a bracket usable for mounting a winch on a pile.

FIG. 7 is a side view of a bracket 700 usable for mounting a winch on a pile 104. The bracket 700 is lowered onto the top edge 702 of pile 104 and into a slot 712 formed in bracket 700 which is sized to enable a secure but removable retention of bracket 700 in place on pile 104. The inside edge of pile 104 is shown at 704 and the outside edge of pile 104 is shown at 706. A winch is mounted to bracket 700 in a conventional manner known in the art at mounting plate 714.

Figure 8:
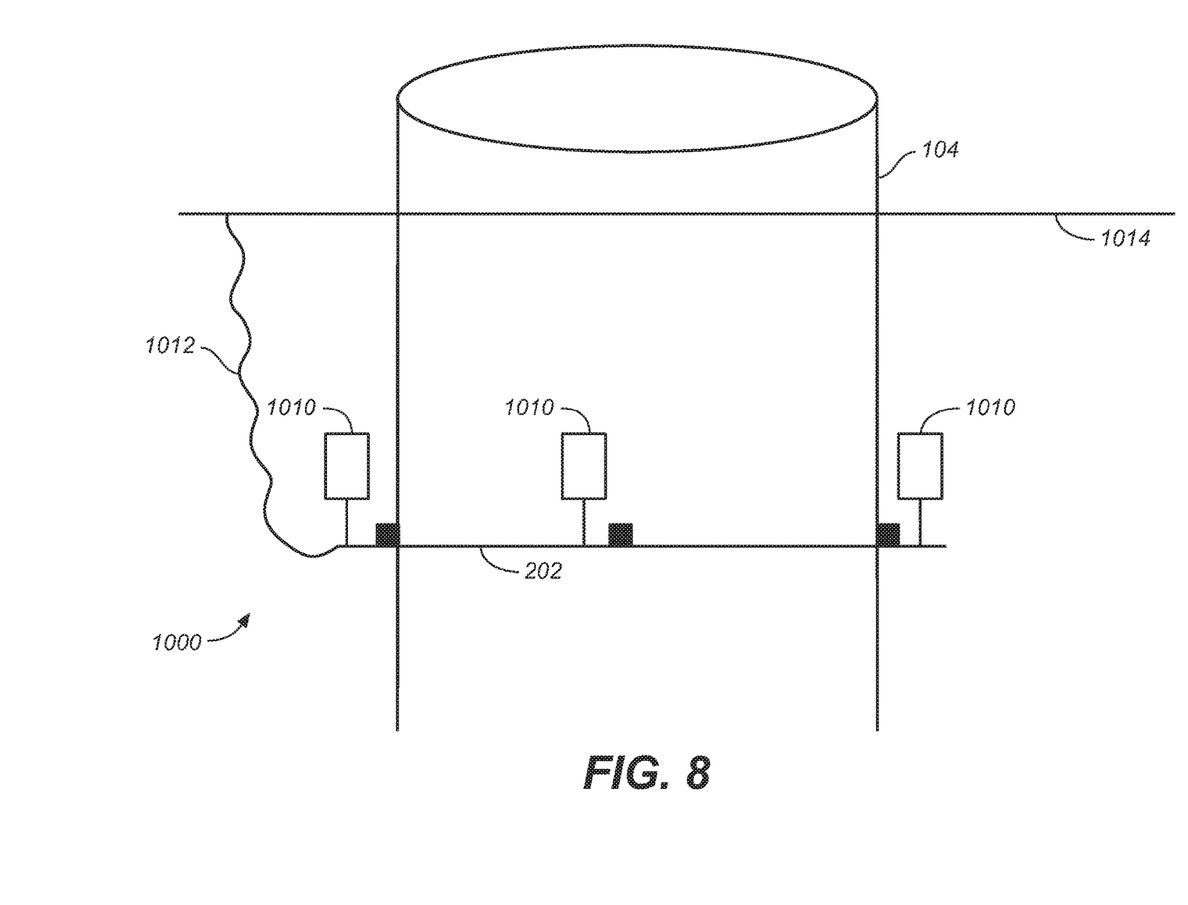
FIG. 8 is another embodiment of the invention that uses thrusters attached to the system frame to cause movement of the system along the vertical surface of a pile.

An exemplary parts list for system 200 is as follows;
2 EA. Warn 1000 AC Winches
⅛" Stainless Steel Cable & Accessories
4 EA. GoPro Hero 4 Black Cameras
4 EA. Sector 9 Downhill skateboard tracks
8 EA. Sector 9 Nine Ball 70 mm Urethane Wheels
8 EA. Sector 9 ABEC 9 Bearings
4 EA. Underwater Kinetics Aqualite Pro 100 lights
1" Stainless Steel Pipe & Fittings FIG. 8 is another embodiment of the invention 1000 that uses thrusters 1010 attached to the system frame 202 to cause movement of the system vertically along the surface of a pile 104. This embodiment may be used in situations where the top of the pile is not accessible for winch mounting. For example, the top of the pile 104 might be supporting a floor 1014 of an offshore oil drilling platform. Consequently, floor 1014 would prevent the system 200 winches from being mounted on top of pile 104. A similar tube structure using stainless steel would be utilized for the frame 202 for mounting of the cameras and underwater lights. The change would be the mounting of a plurality of reversible thrusters 1010 to frame 202 in the form of fans, jets, or compressed air to induce movement of the frame 202 up and down the pile 104 for inspection purposes. A safety line 1012 would preferably also be attached to frame 202 using stainless steel cable, or the like, in order to ensure that, if mechanical failure occurred, there is a method for retrieval of the system 200.

There are a number of other applications for the camera inspection system according to the present invention. A similar system of cameras could be used to inspect tunnels, foundations, pier substructures, piles supporting off-shore rigs and floating structures, vertical poles of any type, bridge footings, and essentially anything in a hazardous-to-human location that would require a visual inspection where the surface of the structure has a consistent geometry along its entire length.

The present invention has been described in relation to particular examples, which are intended in all respects to be illustrative rather than restrictive. Those skilled in the art will appreciate that many different combinations of circuits will be suitable for practicing the present invention. Moreover, other implementations of the invention will be apparent to those skilled in the art from consideration of the specification and practice of the invention disclosed herein. It is intended that the specification and examples therein be considered as exemplary only, with a true scope of the invention being indicated by the following claims.

What is claimed is:

1. A video camera inspection system for remotely inspecting the surface of an underwater pipe or pile comprising:
   a frame sized to move along the length of said pipe or pile;
   a plurality of cameras attached to the frame in spaced apart locations along a plane substantially perpendicular to the axis of the pipe or pile, for enabling video recording of the entire circumference of said pipe or pile as said frame is moved along the pipe or pile;
   a plurality of lights attached to said frame for illuminating the surface of said pipe or pile;

a plurality of wheels attached to said frame sized to provide rolling contact with the surface of the pipe or pile for enabling the cameras to remain a substantially fixed distance from the surface of the pipe or pile and for enabling the frame to move smoothly along the surface of said pipe or pile; and a plurality of cables attached between said frame and a winch system attached to one end of said pipe or pile for enabling the frame to be selectively movable along the length of said pipe or pile, wherein said winch system comprises two winches on opposite sides of the top end of said pipe or pile, and wherein a first one of the said plurality of cables is attached between said first winch and one side of said frame and a second one of said plurality of cables is attached between said second winch and the opposite side of said frame.

2. The system of claim 1, further comprising a plurality of springs mounted between the frame and said wheels to dampen movement of the frame with respect to said pipe or pile, as the frame is moved along the surface of said pipe or pile, to thereby further stabilize the position of the cameras with respect to the surface of said pipe or pile.

3. The system of claim 1, wherein said frame is a circular pipe sized to fit around the pipe or pile, said frame defining a plane substantially perpendicular to the axis of said pipe or pile when said frame is positioned along the length of said pipe or pile, and wherein four cameras are positioned at equidistant locations on said frame.

4. The system of claim 3, wherein said circular pipe is a first circular pipe, said frame further comprising a second circular pipe offset from said first circular pipe, and wherein said wheels are attached to said first circular pipe and said cameras are attached to said second circular pipe.

5. The system of claim 1, wherein said frame has four sides and defines a square shape, said frame sized to fit around the pipe or pile and defining a plane substantially perpendicular to the axis of said pipe or pile when said frame is positioned along the length of said pipe or pile, and wherein a camera and at least one wheel are mounted on each side of said frame.

6. The system of claim 5, wherein each said camera is mounted equidistant from the corners of its respective frame side.

7. The system of claim 5, wherein at least one of the sides of said frame includes two threaded pipe sections for enabling the side to be separated into two parts, for enabling said frame to be positioned around the pipe or pile at a selected point along the length of said pipe or pile.

8. The system of claim 5, further comprising a leg attached on each side of said frame for connecting a respective wheel to said frame, and wherein two wheels are mounted on each said leg, said leg and wheels sized to enable said wheels to contact the surface of said pipe or pile at two points, one on each side of said leg, along the plane of said frame.

9. A video camera inspection system for remotely inspecting the surface of an underwater pipe or pile comprising:

a frame sized to move along the length of said pipe or pile, wherein said frame has four sides and defines a square shape, said frame is sized to fit around said pipe or pile and defining a plane substantially perpendicular to the axis of said pipe or pile when said frame is positioned along the length of said pipe or pile;

a plurality of cameras attached to the frame in spaced apart locations along a plane substantially perpendicular to the axis of the pipe or pile, for enabling video recording of the entire circumference of said pipe or pile as said frame is moved along the pipe or pile;

a plurality of lights attached to said frame for illuminating the surface of said pipe or pile;

a plurality of wheels attached to said frame sized to provide rolling contact with the surface of the pipe or pile for enabling the cameras to remain a substantially fixed distance from the surface of the pipe or pile and for enabling the frame to move smoothly along the surface of said pipe or pile; and a plurality of cables attached between said frame and a winch system attached to one end of said pipe or pile for enabling the frame to be selectively movable along the length said pipe or pile, wherein said winch system comprises two winches on opposite sides of the top end of said pipe or pile, and where a first one of said plurality of cables is attached between said first winch and one corner of said frame and a second one of said plurality of cables is attached between said second winch and an opposite corner of said frame.

10. A video camera inspection system for remotely Inspecting the surface of an object comprising:

a frame sized to move along the length of said object;

a plurality of cameras attached to the frame in spaced apart locations along a plane substantially perpendicular to the axis of the object, for enabling video recording of the entire circumference of said object as said frame is moved along the object;

a plurality of lights attached to said frame for illuminating the surface of said object;

a plurality of wheels attached to said frame sized to provide rolling contact with the surface of the object for enabling the cameras to remain a substantially fixed distance from the surface of the object and for enabling the frame to move smoothly along the surface of said object;

a plurality of remotely controlled reversible thrusters attached to said frame for enabling the frame to be selectively movable along the length of said object; and a safety line attached to said frame to enable retrieval of said system in ease of mechanical failure of said remotely controlled reversible thrusters.

* * * * *